US011517189B2

(12) United States Patent
Golenberg et al.

(10) Patent No.: US 11,517,189 B2
(45) Date of Patent: Dec. 6, 2022

(54) PORTABLE ENDOSCOPE WITH INTERFERENCE FREE TRANSMISSION

(71) Applicants: Lavie Golenberg, Farmington Hills, MI (US); Prem Kumar Sivakumar, Detroit, MI (US)

(72) Inventors: Lavie Golenberg, Farmington Hills, MI (US); Prem Kumar Sivakumar, Detroit, MI (US)

(73) Assignee: Lavie Golenberg, Farmington Hills, MI (US)

( * ) Notice: Subject to any disclaimer, the term of this patent is extended or adjusted under 35 U.S.C. 154(b) by 74 days.

(21) Appl. No.: 17/070,989

(22) Filed: Oct. 15, 2020

(65) Prior Publication Data

US 2021/0045623 A1 Feb. 18, 2021

Related U.S. Application Data

(63) Continuation-in-part of application No. 14/411,877, filed as application No. PCT/US2013/048515 on Jun. 28, 2013, now abandoned.
(Continued)

(51) Int. Cl.
*A61B 1/05* (2006.01)
*A61B 1/06* (2006.01)
(Continued)

(52) U.S. Cl.
CPC ............ *A61B 1/05* (2013.01); *A61B 1/00009* (2013.01); *A61B 1/042* (2013.01); *A61B 1/0684* (2013.01); *G02B 23/125* (2013.01)

(58) Field of Classification Search
CPC combination set(s) only.
See application file for complete search history.

(56) References Cited

U.S. PATENT DOCUMENTS

| 6,768,496 | B2 | 7/2004 | Bieger | A61B 90/36 345/630 |
| 2005/0012869 | A1* | 1/2005 | Akiyama | H04N 21/43637 725/127 |

(Continued)

FOREIGN PATENT DOCUMENTS

| EP | 1847214 A2 | 10/2007 |
| JP | 4261148 B2 | 4/2009 |

(Continued)

OTHER PUBLICATIONS

Golmie, N. et al., "Interference Evaluation of Bluetooth and IEEE 802.11b Systems", Wireless Networks, May 2003, pp. 201-211, vol. 9, Issue 3, © 2003 Kluwer Academic Publishers.
(Continued)

*Primary Examiner* — Joon Kwon
(74) *Attorney, Agent, or Firm* — Blue Filament Law PLLC

(57) ABSTRACT

An endoscope that integrates the functions of an optical tower into a portable device, while eliminating the use of cords or cables that carry light, video signals or images, and power to the endoscope that may conflict with the movement of a surgeon and the members of the surgical team, or other operators in non-medical related applications is provided. The endoscope incorporates a camera, an image processor, a light source, a transmitter, a communication interface, a control interface, and one or more of a power source in a single portable unit or enclosure. The camera is in electrical communication with the image processor and supplies images and video to the image processor obtained via an elongated endoscope tube. The light source illuminates a viewing field of the endoscope via the elongated tube.

19 Claims, 3 Drawing Sheets

Related U.S. Application Data

(60) Provisional application No. 61/665,877, filed on Jun. 28, 2012.

(51) Int. Cl.
  A61B 1/04 (2006.01)
  G02B 23/12 (2006.01)
  A61B 1/00 (2006.01)

(56) References Cited

U.S. PATENT DOCUMENTS

| | | | |
|---|---|---|---|
| 2005/0085690 A1* | 4/2005 | Tien | A61B 1/042 |
| | | | 348/E7.087 |
| 2005/0148854 A1* | 7/2005 | Ito | A61B 90/36 |
| | | | 600/407 |
| 2005/0196023 A1* | 9/2005 | Chen | A61B 1/041 |
| | | | 382/128 |
| 2006/0293563 A1 | 12/2006 | Banik et al. | |
| 2008/0091302 A1 | 4/2008 | Sholev | |
| 2009/0003964 A1 | 1/2009 | Keener et al. | |
| 2009/0058997 A1* | 3/2009 | Kato | H04N 5/23203 |
| | | | 348/E7.085 |
| 2009/0192519 A1 | 7/2009 | Omori | |
| 2009/0209810 A1* | 8/2009 | Endo | A61B 1/00016 |
| | | | 600/109 |
| 2010/0141744 A1 | 6/2010 | Amling et al. | |
| 2012/0071721 A1 | 3/2012 | Remijan et al. | |
| 2012/0162401 A1* | 6/2012 | Melder | H04N 7/183 |
| | | | 348/E7.085 |
| 2013/0034825 A1* | 2/2013 | Phillips | A61B 1/00183 |
| | | | 433/29 |
| 2013/0137377 A1* | 5/2013 | Endo | A61B 1/00016 |
| | | | 455/66.1 |
| 2015/0297062 A1* | 10/2015 | Golenberg | A61B 1/00018 |
| | | | 348/68 |

FOREIGN PATENT DOCUMENTS

| | | |
|---|---|---|
| JP | 4937136 B2 | 5/2012 |
| KR | 101119585 B1 | 3/2012 |

OTHER PUBLICATIONS

Pandya, Abhilash "Medical Augmented Reality System for Image-Guided and Robotic Surgery: Development and Surgeon Factors Analysis" Dissertation submitted to the Graduate School of Wayne State University, Detroit, Michigan; 2004; pp. 1-171.

Abstracts on Endoscopy Surgery From the Conference Preceding—"Second World Conference of the International Study Group on Neuroendoscopy (ISGNE)", Castel Dell'Ovo, Naples, Italy, Sep. 11-13, 2003; Child's Nerv Syst (2003) 19:687-709; pp. 687-709; © Springer-Verlag 2003.

* cited by examiner

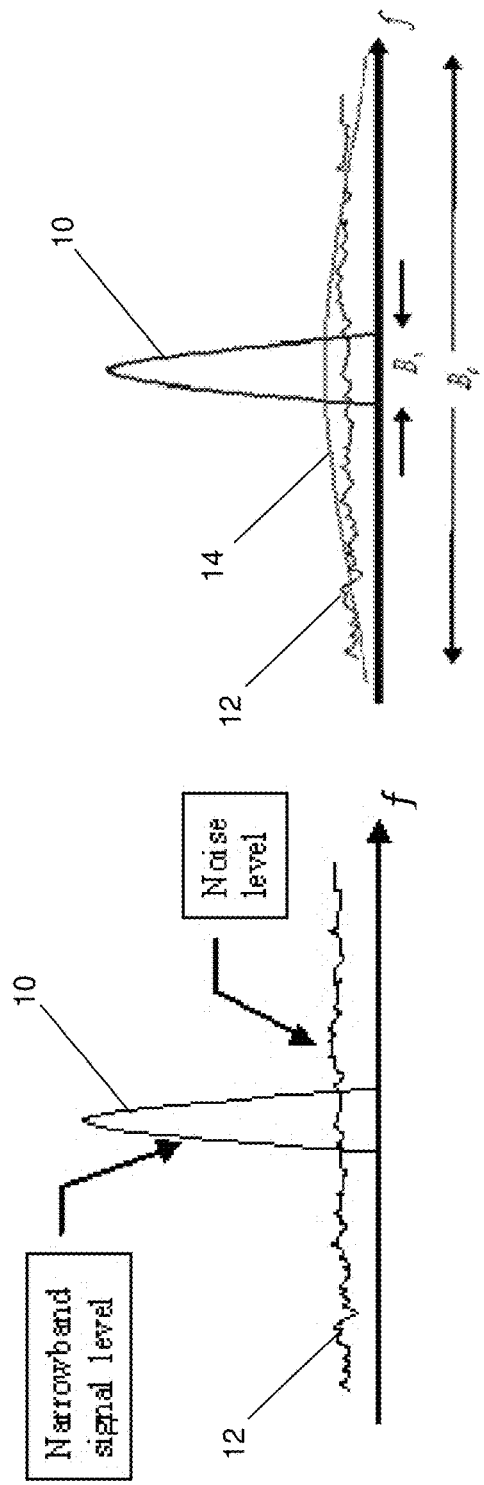
FIG. 1A (Prior Art)
FIG. 1B (Prior Art)
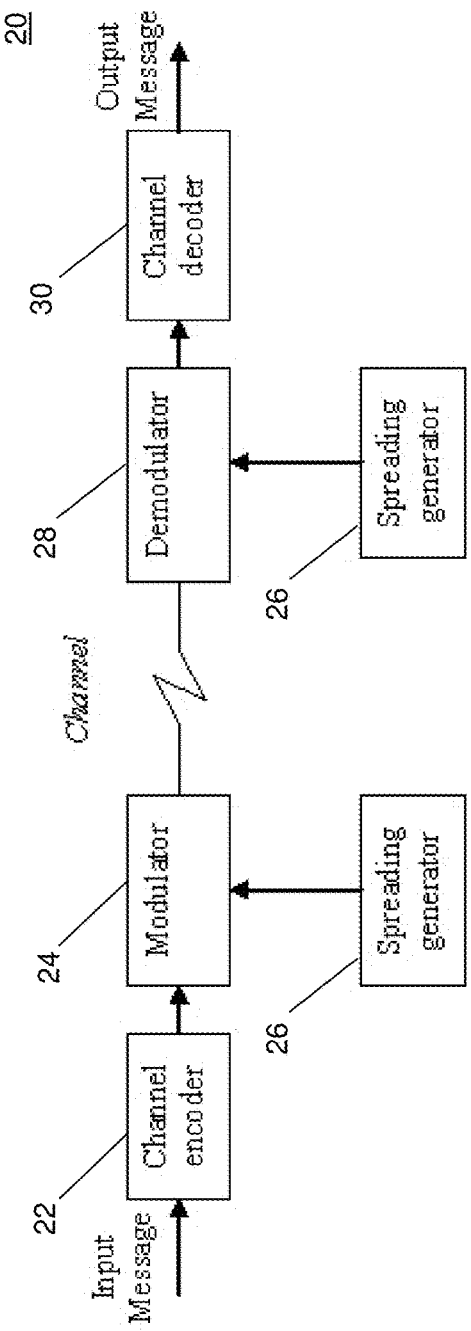
FIG. 2 (Prior Art)

PORTABLE ENDOSCOPE WITH INTERFERENCE FREE TRANSMISSION

CROSS-REFERENCE TO RELATED APPLICATION

This application is a continuation-in-part of claims priority of U.S. patent application Ser. No. 14/411,877, filed Dec. 29, 2014, which is a US National Stage Entry of PCT/US2013/048515, filed Jun. 28, 2013, which in turn claims priority benefit of U.S. Provisional Application Ser. No. 61/665,877, filed Jun. 28, 2012; which is incorporated herein by reference.

FIELD OF THE INVENTION

The present invention in general relates to medical and inspection devices and in particular to a wireless portable endoscope with integrated power, lighting, and video processor.

BACKGROUND OF THE INVENTION

An endoscope is a device with a light attached to one end, used to look inside or inspect a region inside a confined area or a specific body cavity or organ. Endoscopes are inserted through a natural opening, such as the mouth or rectum and are commonly used to detect ulcers, inflammation, erosions, polyps, strictures, malignancies, varices, and bleeding sites. In a surgical procedure, an endoscope is inserted through a small incision that permits minimally invasive procedures that improve patient care and minimize recovery time. Any medical procedure that uses endoscope equipment is called an endoscopy. Particular medical procedures that employ endoscopes include arthroscopy (orthopedic joints), bronchoscopy (lung), colonoscopy (colon), cystoscopy (bladder), gastroscopy (upper gastrointestinal tract), laryngoscopy (larynx), laparoscopy (abdomen, peritoneal cavity, ovaries, fallopian tubes and uterus), nephroscopy (kidney), otoscopy (ear), and rhinoscopy (nose).

Endoscopes capture images through a long tube, which can be rigid or flexible. Images may be captured by a purely fiber optic scope with a bundle of glass fibers that collect the lighted images at one end and transfer them to an eye piece, or video images may be obtained using a small, optically sensitive computer chip at the end of the scope. The computer chip transmits electronic signals up the scope to a computer which then displays the image on a large video screen. Advances in lighting technologies, such as light emitting diodes (LED) have improved the imaging performance of endoscopes. Additional instruments for cutting, grasping and other functions are often attached to the endoscope, or are supplied via an open channel in the endoscope to allow other instruments to pass through in order to perform biopsies, remove polyps or inject solutions, as needed. Endoscopes are also well suited for a number of industrial applications such inspections and are synonymously referred to herein as borescopes.

While endoscopes offer many advantages to physicians and patients, the use of current endoscopes require the use of an optical tower. Optical towers include a power source for the endoscope, a monitor/display, a light source, and a video receiver and processor. Optical towers are generally quite large, and take up valuable floor space in an operating room. In addition, the use of cords or cables that carry light, video signals or images, and power to the endoscope interfere with the movement of the surgeon and the members of the surgical team.

Modern operating rooms and surgical theaters, even in remote locations, have several electrical and mechanical instruments, as well as data gathering electronics that potentially generate electromagnetic and radio wave interference. These sources of interference can potentially disrupt data transmission from surgical diagnostic devices such as endoscopes.

Spread Spectrum refers to a system that spreads a signal over a large frequency band thereby providing a secure communication signal that is also more robust and impervious to potential sources of signal interference, signal jamming, and unauthorized eavesdropping and signal interception. FIG. 1A illustrates a frequency spectrum (domain) view of a narrowband signal 10 with respect to a random noise floor 12. The narrowband signal 10 is easily isolated from the random noise floor 12, and is easily jammed by any other signal in the same band. Likewise, the narrowband signal 10 is easy to detect and can also be intercepted since the frequency band is fixed and narrow. FIG. 1B illustrates a frequency spectrum view of the narrowband signal 10 of FIG. 1A converted to a spread spectrum signal 14 in relation to the random noise floor 12. The spread spectrum signal 14 uses more bandwidth than the original message of the narrowband signal 10 while maintaining the same signal power. A spread spectrum signal does not have a clearly distinguishable peak in the spectrum, which makes the signal more difficult to distinguish from noise and therefore more difficult to jam or intercept. Furthermore, an interfering signal in a specific frequency will have little to no impact on the spread spectrum signal.

FIG. 2 is a block diagram of a spread spectrum communication system 20. An input message is encoded to a series of pulses with a channel encoder 22 that in turn control a modulator 24 which is combined with a spreading generator 26 to produce the transmitted spread spectrum signal. At the receiving end, the demodulator 28 using a decryption or synchronization key from the spreading generator 26 the series of pulses obtained from the demodulated signal are provided to the channel decoder 30 to obtain the an output message that corresponds to the input message. There are two predominant techniques to spread the spectrum communications: frequency hopping and direct sequence. Frequency hopping involves a narrow band signal jumping in random narrow bands within a larger bandwidth. Direct sequence which introduces rapid phase transitions to the data to make the data have a larger in bandwidth in the frequency domain. Direct sequence spread spectrum technique is the predominantly used in the industry as code division multiple access (CDMA), Universal Mobile Telecommunications Service (UMTS), and 802.11 wireless standard. The advantages of spread spectrum include enhanced privacy and secure communications because a signal is "hidden" like noise, non-interference with other signals in the same band, the possibility to share frequency and time at the same time (CDMA), and protection against jamming.

While there have been many advancements in endoscopes, there exists a need for an endoscope that integrates the functions of an optical tower into a portable device, while providing the flexibility eliminating the use of cords or cables that carry light, video signals or images, and power to the endoscope that may conflict with the movement of a surgeon and the members of the surgical team. There is a further need for interference free transmission of image data from the endoscope.

SUMMARY OF THE INVENTION

An endoscope with secure and interference free data signals is provided that integrates the functions of an optical tower into a portable device, while eliminating the use of cords or cables that carry light, video signals or images, and power to the endoscope that may conflict with the movement of a surgeon and the members of the surgical team, or other operators in non-medical related applications is provided. Embodiments of the inventive endoscope incorporate a camera, an image processor, a light source, a transmitter, a communication interface, a control interface, and a power source in a single portable unit or enclosure. The camera is in electrical communication with the image processor and supplies images and video to the image processor obtained via an elongated endoscope tube. The light source illuminates a viewing field of the endoscope via the elongated tube. Spread spectrum communication techniques are employed for wireless transmission of data from the endoscope to provide a signal that is robust and impervious to sources of interference and conflicting signals. One or more power sources supply power to the camera, the image processor, the light source, and the transmitter.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1A illustrates a frequency spectrum view of a narrowband signal with respect to a random noise floor;

FIG. 1B illustrates a frequency spectrum view of the narrowband signal of FIG. 1A converted to a spread spectrum signal in relation to the random noise floor;

FIG. 2 is a prior art block diagram of a spread spectrum system illustrating subsystems for transmission and receiving of a signal;

DETAILED DESCRIPTION OF THE PREFERRED EMBODIMENTS

Figure 3:
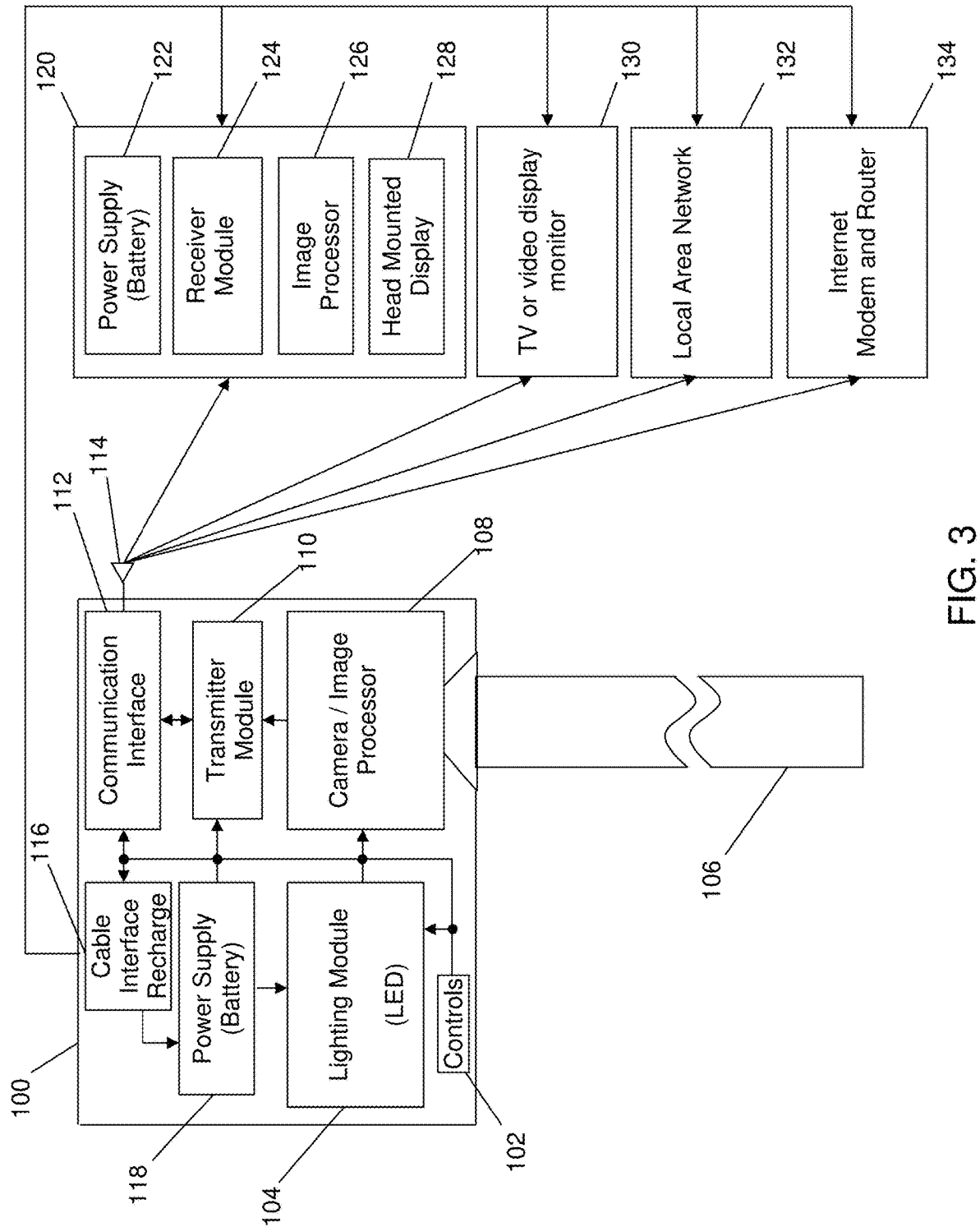
FIG. 3 illustrates a block diagram of an embodiment of the endoscope in communication with various user and network devices.

The present invention has utility as an endoscope with secure and interference free data signals that integrates the functions of an optical tower into a portable device, while eliminating the use of cords or cables that carry light, video signals or images, and power to the endoscope that may conflict with the movement of a surgeon and the members of the surgical team, or other operators in non-medical related applications. Spread spectrum communication techniques may be employed for wireless transmission of data from the endoscope to provide a signal that is robust and impervious to sources of interference and conflicting signals. Embodiments of the inventive endoscope incorporate a camera, an image processing unit, a light source, a transmitter, a communication interface, a control interface, and a power source in a single portable unit or enclosure.

Embodiments of the inventive endoscope eliminate the need for an optical tower that traditionally provides a power source, monitor, light source, and video processing. The inventive endoscope is a compact and inexpensive tool for performing endoscopic surgery by eliminating the optical tower currently used for endoscopic surgery. Embodiments of the medical hardware invention saves space through the elimination of the optical tower, and as a result provides surgeons with the flexibility and option to perform endoscopic based surgery in a smaller operating room of a clinic or office setting. It is appreciated that the endoscope is well suited for field hospital usage. The inventive endoscope affords portability, since an optical tower is not necessary for the operation of embodiments of the endoscope, and endoscopic surgery can now be performed anywhere that has carbon dioxide gas, a power source for cauterization, and anesthesia. The reduced size, light weight, and robust construction of the portable endoscope allows the device to be handheld or fixed to a mechanical or robotic arm. It is further noted that since all components of an optical tower are now integrated into the inventive device, the components are all able to cleaned through the same fashion as an endoscope or laparoscope.

The inventive endoscope has potential uses for the military and non-governmental agencies that provide medical care in a mobile facility with limited facilities. In addition, embodiments of the invention can also be used in smaller or rural facilities that cannot designate a room purely for endoscopic surgery. Furthermore, the portability of the inventive endoscope allows for non-medical related applications such as industrial inspection, pest control, and remediation, etc.

As previously noted, the reduction in size and portability of embodiments of the inventive endoscope makes the device amenable to use in field hospitals. However in the field, embodiments of the endoscope may be subjected to unpredictable electromagnetic and radio frequency interferences in the surrounding area of use, which may not be a problem in a hospital setting using immobile equipment. For example, in a practical use setting that illustrates the advantages of embodiments of the inventive endoscope, as an injured patient is being transported to an emergency room in a helicopter flying over variable terrain, first responders can perform an endoscopic procedure en route to assess the patient's injuries and if needed open an airway or stop critical hemorrhaging. Images and video of such an en route endoscopic procedure can be vitally important for determining a lifesaving course of action for both the first responders and possible communication to remote emergency room personnel. However, this lifesaving value creates a problem not encountered by the prior art endoscopic devices designed for use in the electronic signal protected confines of hospitals and other fixed medical facilities, namely "interfering signals" that disrupt reliable transmission of the endoscopic data to a remote location. In contrast to the controlled environments of fixed medical facilities, these "interfering signals" abound in the environment during the helicopter flight in which the claimed endoscope is in use. For example, "interfering signals" may come from cellular towers, radio or television broadcasting equipment, WIFI networks, air traffic control towers, emergency services communication networks, and more; any number of which are randomly encountered during the helicopter flight to the hospital emergency room.

In order to overcome radio frequency interference in a field environment, and for poorly grounded or shielded equipment in an operating room (OR) environment, specific embodiments of the endoscope may employ spread spectrum communication techniques for wireless transmission of data from the endoscope to provide a signal that is robust and impervious to sources of interference and conflicting signals.

In certain inventive embodiments, images and video provided by the inventive endoscope are transmitted simultaneously either wirelessly or via a wired connection to personal wearable viewers equipped with heads up display (HUD), the Internet via a router, local area networks (LAN), and other configurable or available forms of communication. In other inventive embodiments, the endoscopic imagery is also readily viewed on a television (TV) screen if broadcasted on a specific frequency. In some inventive embodiments, a user manually selects transmission frequencies and video channels for the endoscope to account for interfering signals. In addition, a user may be able to switch video channels to access additional informational content or operating room views. A TV adapter is included in some inventive embodiments to provide direct transmission. The ability to send images over networks is beneficial to surgeons not in the operating room that are needed for consultations, educational purposes, as well as remote viewers for non-medical applications. The innovation provided by embodiments of the invention allows a surgeon to keep a headset, video monitor, or remote viewing device in their office, home or other remote location, allowing for quick feedback rather than have the surgeon physically travel to the operating room to provide surgical consultation.

In other inventive embodiments, a user has the option of providing manually selectable transmission frequencies and video channels for the endoscope to account for interfering signals. In addition, a user may be able to switch video channels to access additional informational content or operating room views. In still other inventive embodiments, the capability to overlay images onto the endoscope's video feed from another source or piece of medical equipment or monitoring device is provided. Overlaid images illustratively include patient vital sign information, augmented reality images, scans from computed tomography (CT), ultrasound images, Doppler flow scans, X-ray, magnetic resonance imaging (MRI), or combinations thereof.

With embodiments of the inventive endoscope, the insertion of and design of surgical tools will remain the same. Trocars are still required to provide the seal for the hand tools and endoscope, and the hand tools are powered for cauterization. While a surgeon manipulates the hand tools, and another surgeon often navigates the endoscope. The electronics (camera and imager, transmitter, lighting, communication interface, power supply) are mounted onto the endoscope in the same manner that the endoscope video camera was mounted onto existing endoscope designs. A light source, including light emitting diodes (LED), is attached to the inventive endoscope by a fiber-optic cable. In certain inventive embodiments, a visual record of the viewing field of the endoscope is collected, and transmitted via wired or wireless signals to personal video viewers worn by the master surgeon manipulating the hand tools and by the surgeon navigating the endoscope. It is appreciated that in specific inventive embodiments, it is beneficial to have the capability to transmit endoscopic imagery to a TV, especially from remote locations with limited communications infrastructure. This added flexibility would still not require the optical tower common to conventional systems and provides and optional backup in cases where the HUD is not functioning. Additional wired/wireless signals can be transmitted to additional surgeons, nurses, students, and observers as necessary. In non-medical applications, the video features of the inventive endoscope may be used for inspection of remote or hard to reach areas that include, for example, industrial inspection, pest control, remediation such as in pipes, sewers, machinery enclosures, and nuclear facilities. Military and public safety agencies may use the video features for reconnaissance and rescue missions. The user's ability to switch video channels allows a soldier or emergency personnel to see via shared views what their teammates see from their own endoscopes, whether their teammate is alive or dead, providing a higher level of situational awareness. It is appreciated that the switchable video channels may be transmitted using spread spectrum communication techniques known in the art.

With reference to the attached figures, an inventive endoscope is depicted generally at 100 in FIG. 3. The endoscope 100 includes within an integrated enclosure with optical tower function so as to eliminate the need of an optical tower. Controls 102 are present in the endoscope 100 in electrical communication with lighting module 104, camera/image processor 108, transmitter module 110, and communication interface 112. Controls 102 provide the user with the ability to control the intensity of the lighting with the lighting module 104, camera and imaging parameters of the camera/image processor 108, as well as communication parameters of the transmitter module 110 and communication interface 112. The lighting module 104 provides light via elongated tube 106 to the surgical area of interest with controlled intensity and apertures. Camera and image parameters illustratively include depth of field, frame rate, illumination wavelengths, focus, pixel density, false color, frame size (x/y ratio), noise filtering, and baud rate. The elongated tube 106 can be rigid or flexible, as are conventional to the art. In certain inventive embodiments, images may be captured by a purely fiber optic scope with a bundle of glass fibers that collect the lighted images at one end of the elongated tube 106 and transfer them to an eye piece, or video images may be obtained using a small, optically sensitive computer chip, such as a charged coupled device (CCD) within the camera/image processor 108 at the end of the scope tube 106.

The scope tube 106 besides providing a conduit for collecting images and a pathway for insertion of surgical tools is provided in certain inventive embodiments with a channel for providing suction to an examined area to remove obstructions such as smoke or liquids, or to remove materials such as masses of tissue that are being excised or debulked in a surgical procedure. In addition, the scope tube 106 is provided with a channel to introduce a fluid to a remote tissue area for example a liquid active agent, such as a curable resin, irrigation fluid, air, is provided via the channel to the tissue. Furthermore, other operations that may be conducted via scope tube 106 illustratively include the insertion of a spectroscopy system or the introduction of a manipulator or thermal tools such as an induction heating coil, welding gases (in an industrial pipe testing/repair setting), or cautery tool.

The transmitter module 110 broadcasts the images and video obtained from the camera/image processor 108 via predefined frequencies and protocols including CDMA, UMTS, WiFi (802.11 a,b,g,n), WiMax, Bluetooth®, near field, cellular protocols, and other existing and contemplated communication protocols. As previously described, many of the aforementioned communication protocols are based on spread spectrum communication techniques including frequency hopping and direct sequence. In certain inventive embodiments of the transmitter module 110 may also allow for user manual selectable transmission frequencies and video channels for the endoscope to account for interfering signals. In addition, a user may be able to switch video channels to access additional informational content or operating room views. In other embodiments, the transmitter module 110 provides the capability to overlay images from another source or piece of medical equipment or monitoring device onto the endoscope video feed via a wired or wireless connection to the overlay source. In inventive embodiments, the user may be able to switch between visualization options that provide a surgeon with flexibility of having the choice to switch between modalities (not just channels) such as Bluetooth®, radio (TV), HDMI, USB, etc.

In another inventive embodiment, the transmission from the endoscope is encrypted for instances where secure communications are required. The communication interface 112 routes the broadcast signals to an antenna 114, or takes the camera and image signals and routes them to a cable interface 116 for a wired connection via for example composite video, s-video, universal serial bus (USB), high definition media interface (HDMI), digital video interface (DVI), coax cable, or other wired standards. Power supply 118 may be directly connected to a 110-240 V AC electrical outlet, or may be a battery that is or is not rechargeable. A rechargeable battery may be charged while connected to an outlet, or via a communication cable such as a USB cable. Power supply 118 may act as a power source or supply to peripheral devices, such as a vacuum for suction or other medical assist devices, via a USB connector or DC power receptacle. In specific inventive embodiments the power supply 118 may automatically switch from a rechargeable battery to a wired power cord when the battery is running low. An audible tone may be emitted by the endoscope device 100 to notify the user that the battery is running low. As noted above, embodiments of the inventive endoscope are portable self-contained units that are configured for wired or wireless operation thereby eliminating the need for an optical tower.

The endoscope 100 may be in wired- or wireless-contact with personal viewer 120. Personal viewer 120 is readily configured with a self-contained power supply 122 such as a battery, a receiver module 124 for receiving the wired or wireless signals, an image processor 126 for translating the received signals to one or multi-dimensional views in a head mounted display or heads up display (HUD) 128 or TV or video display monitor 130. Signals are readily sent via wired- or wireless-communication to a local area network (LAN) 132 such as by Ethernet for internal communication systems. In addition signals from the endoscope 100 may be transmitted to an Internet modem and/or router 134 for computers and other data devices to access the patient images taken by the endoscope 100 anywhere in the world via wide area networks (WAN), WiFi, WiMAX, satellite, cellular telephone network, or other known or available wireless network connections.

Procedures conducted with the endoscope may be recorded for purpose of teaching, liability, research, etc. The procedural data may be sent wirelessly to the cloud or a hospital network for storing within the system. In addition, removeable memory cards or USB or wireless hard drives may be connected to the endoscope for collecting data.

Figure 4:
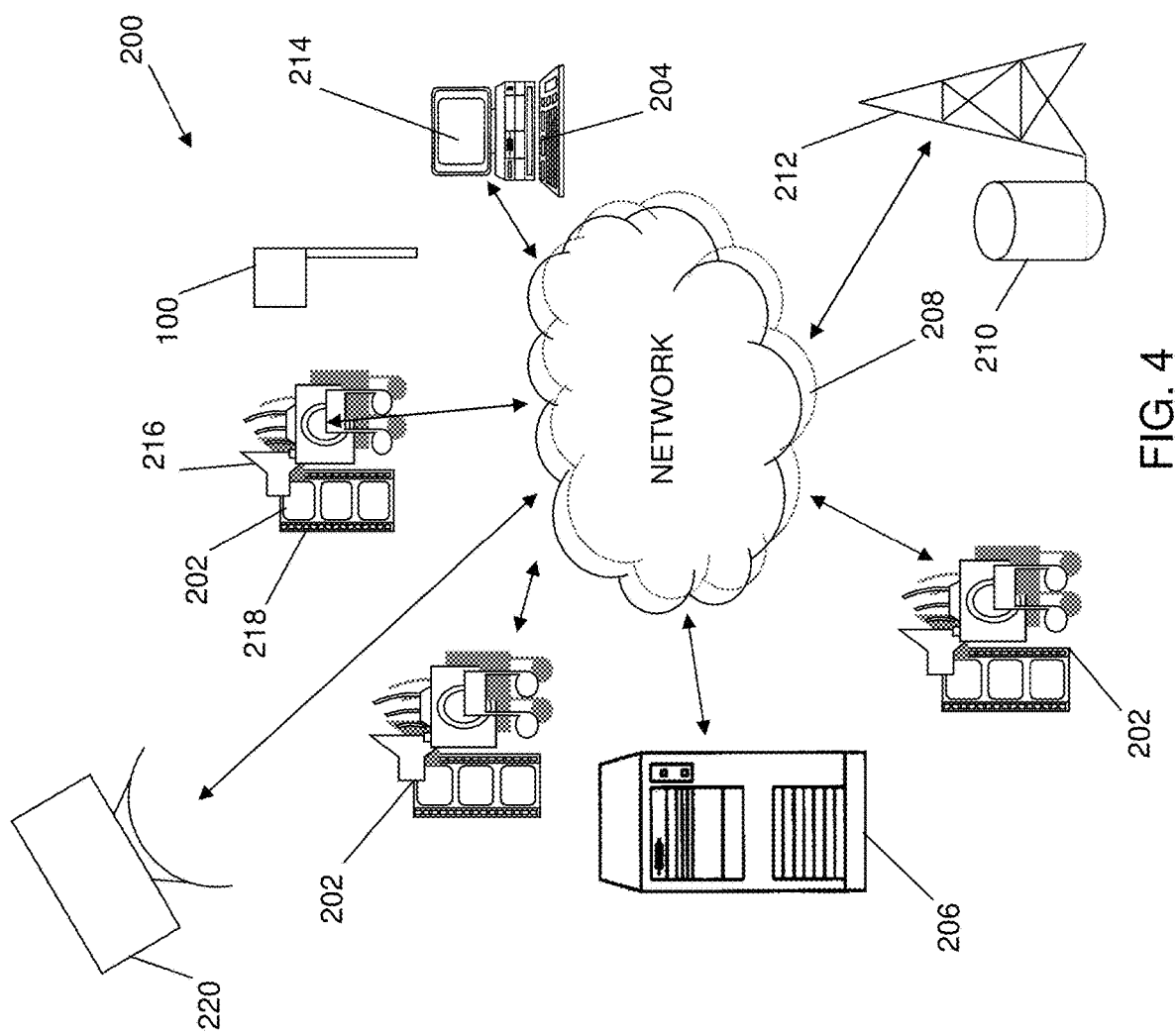
FIG. 4 is a schematic diagram illustrating an overall view of communication devices, computing devices, and mediums for interfacing with the inventive endoscope.

FIG. 4 is a schematic diagram illustrating an overall view of communication devices, computing devices, and mediums for interacting with the endoscope according to embodiments of the invention. The elements of the embodiments of the endoscope in FIG. 3 are included in the networks and devices of FIG. 4

The system 200 includes endoscope 100, the endoscope 100 including within an integrated enclosure optical tower function so as to eliminate the need of a separate optical tower, multimedia devices 202 and desktop computer devices 204 configured with display capabilities 214. The multimedia devices 202 illustratively include mobile communication and entertainment devices, such as cellular phones, mobile computing devices, tablet, TV, and personal displays that are wirelessly connected to a network 208. The multimedia devices 202 have video displays 218 and audio outputs 216. The multimedia devices 202 and desktop computer devices 204 are readily configured with internal storage, software, and a graphical user interface (GUI) for controlling and viewing images from the endoscope 100 according to embodiments of the invention. The network 208 is any type of known network including a fixed wire line network, cable and fiber optics, over the air broadcasts, satellite 220, local area network (LAN), wide area network (WAN), global network (e.g., Internet), intranet, etc. with data/Internet capabilities as represented by server 206. Communication aspects of the network are represented by cellular base station 210 and antenna 212. It is appreciated that the network 208 is in certain inventive embodiments a LAN and each remote device 202 and desktop device 204 executes a user interface application (e.g., Web browser) to contact the server system 206 and or endoscope 100 through the network 208. Alternatively, the remote devices 202 and 204 may be implemented using a device programmed primarily for accessing network 208 such as a remote client.

The software for viewing information from the endoscope 100 of embodiments of the invention, may be resident on the individual multimedia devices 202 and desktop computers 204, or stored within the server 206 or cellular base station 210. Server 206 may implement a cloud-based service for implementing embodiments of the endoscope with a multi-tenant database for storage of separate client data.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An endoscope integrating functionality of an optical tower comprising:
    an elongated endoscope tube adapted for insertion into a confined surgical field and with a channel therein for suction extending therethrough;
    an enclosure integrating the functionality of the optical tower without the optical tower being separately present and cords that carry light, video signals or images, or power between said enclosure and the optical tower, said enclosure containing;
        a camera having imaging parameters of depth of field, frame rate, illumination wavelengths, focus, pixel density, false color, frame size (x/y ratio), noise filtering, and baud rate;
        an integrated image processor, said camera in electrical communication with said integrated image processor and supplies images and video to said image integrated processor obtained via said elongated endoscope tube for display on a head mounted display, heads up display (HUD), TV if the images are broadcasted on a specific frequency, video display monitor, mobile computing devices, cellular phone, tablet, or mobile communication and entertainment devices;

a light source, illuminating a viewing field of said endoscope tube with controlled intensity and apertures via said elongated tube, said elongated tube in optical communication with said enclosure and extending therefrom with collected lighted images being transferred to said image processor;

a transmitter module employing automatic spread spectrum communication transmission of user selectable video channels, said transmitter module engaging in frequency hopping over a band of frequencies to account for interfering signals, and for overlay of images onto a video feed from said camera that are from another source or piece of medical equipment or monitoring device via a wired or wireless connection to the transmitter module, wherein said transmitter module is switchable between two or more video channels to access shared views between two or more additional users operating additional endoscopes via said image processor for display on said head mounted display, heads up display (HUD), TV, video display monitor, mobile computing devices, cellular phone, tablet, or mobile communication and entertainment devices;

a communication interface;

a control interface; and one or more of a power source, said one or more of said power source supplies powering said camera, said image processor, said light source, and said transmitter module and the suction; and a personal viewer with a self-contained power supply for receiving the wired or wireless signals, a personal image processor for translating the received signals to one or multi-dimensional views in said head mounted display or heads up display (HUD) or said TV or video display monitor.

2. The endoscope of claim 1 wherein said controls interface provides a user with the ability to control at least one of lighting intensity with said lighting module, said camera, parameters of imaging, communication parameters of said transmitter module and said communication interface.

3. The endoscope of claim 1 wherein the images are captured via a bundle of glass fibers that collect at a distal end of said elongated tube and provide the images to said camera and image processor at the proximal end of said elongated tube.

4. The endoscope of claim 1 wherein said transmitter module broadcasts the images and video obtained from said camera and image processor via predefined frequencies and protocols comprising at least one of WiFi, WiMax, near field, wide area networks (WAN), satellite, Internet, or cellular.

5. The endoscope of claim 4 wherein said broadcasts are encrypted.

6. The endoscope of claim 1 wherein said communication interface routes the broadcast signals to an antenna.

7. The endoscope of claim 1 wherein said communication interface takes the image and videos and routes the image and videos to a cable interface for a wired connection.

8. The endoscope of claim 7 wherein the wired connection comprises at least one of composite video, s-video, universal serial bus (USB), high definition media interface (HDMI), digital video interface (DVI), or coax cable.

9. The endoscope of claim 1 wherein said transmitter module is switchable between two or more video channels to access additional informational content or operating room views via said image processor for display on said head mounted display, heads up display (HUD), TV, video display monitor, mobile computing devices, cellular phone, tablet, or said mobile communication and entertainment devices.

10. The endoscope of claim 1 wherein the overlay images represent at least one of patient vital sign information, augmented reality images, scans from computed tomography (CT), x-ray, ultrasound images, Doppler flow scans, X-ray, or magnetic resonance imaging (MRI).

11. The endoscope of claim 1 wherein said power supply is directly connected to an AC electrical outlet.

12. The endoscope of claim 1 wherein said power supply is a battery.

13. The endoscope of claim 12 wherein said battery is rechargeable, said rechargeable battery is charged while connected to an outlet, or via a communication cable.

14. The endoscope of claim 1 wherein said endoscope is in wired or wireless contact with one or more personal viewers configured with a heads up display (HUD).

15. The endoscope of claim 1 wherein said endoscope is in wired or wireless contact with one or more presentation devices of a tablet, computer monitor, cell phone, or a television.

16. The endoscope of claim 1 further comprising a conduit.

17. The endoscope of claim 1 wherein said one or more of said power source supplies act as a power source to peripheral devices, including, but not limited to, a vacuum device or other medical assist devices, via a USB connector or DC power receptacle built in to said enclosure.

18. The endoscope of claim 1 wherein said light source is a light emitting diode (LED).

19. The endoscope of claim 1 wherein said transmitter module engages in channel switching via Bluetooth.

* * * * *